United States Patent
Ugwuegbulam et al.

(10) Patent No.: US 6,479,660 B1
(45) Date of Patent: Nov. 12, 2002

(54) PROCESS FOR THE PREPARATION OF ANTI-MALARIAL DRUGS

(75) Inventors: Cletus Onwuzurike Ugwuegbulam, Stevenage (GB); James Edward Foy, Dresher, PA (US)

(73) Assignees: SmithKline Beecham p.l.c., Brentford (GB); SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/051,571

(22) PCT Filed: Oct. 11, 1996

(86) PCT No.: PCT/EP96/04433
§ 371 (c)(1),
(2), (4) Date: Dec. 14, 2001

(87) PCT Pub. No.: WO97/13753
PCT Pub. Date: Apr. 17, 1997

(30) Foreign Application Priority Data

Oct. 13, 1995 (GB) .............................. 9521004

(51) Int. Cl.$^7$ ...................... C07D 215/16; A61K 31/47
(52) U.S. Cl. ...................................... 546/153; 514/312
(58) Field of Search ........................... 546/157; 514/312

(56) References Cited

U.S. PATENT DOCUMENTS 4,431,807 A * 2/1984 Strube
4,617,394 A 10/1986 Blumbergs et al.

OTHER PUBLICATIONS

CA 123:217615, Karle, 1995.*
CA 106:119703, Blumbergs, 1996.*
Nodiff, et al., "Modifications of a Primaquine as Antimalarials. 3. 5–Phenoxy Derivatives of Primaquine", *J. Med. Chem.*, vol. 25: pp. 1097–1101, (1982).
Chen, et al., "Modifications of a Primaquine as Antimalarials. 1. 5–Phenoxy Dervatives of Primaquine", *J. Med. Chem.*, vol. 20, No. 8: pp. 1107–1109, (1977).
LaMontagne, et al., "Antimatarials. 14. 5–(Aryloxy)–4–methylprimaquine Analogues. A Highly Effective Series of Blood and Tissue Schizonticidal Agents", *J. Med. Chem.*, vol. 25: pp. 1094–1097, (1992).
Carroll, et al., "4–Substituted 5–[m–(Trifluoromethyl) phenoxy] Primaquine Analogues as Potential Antimalarial Agents", *J. Med. Chem.*, vol. 28: pp. 1564–1567, (1985).

* cited by examiner

Primary Examiner—D. Margaret Seaman
(74) Attorney, Agent, or Firm—Kathryn L. Sieburth; Mary E. McCarthy; Charles M. Kinzig

(57) ABSTRACT

The invention relates to novel intermediates and processes for the preparation of quinoline compounds useful as anti-malarial drugs and novel intermediates useful in the process. A process for the preparation of a compound of formula (I) in which $R^1$ is $C_{1-6}$ alkyl; $R^2$ and $R^3$ are independently hydrogen, halogen, trifluoromethyl or $C_{1-6}$ alkoxy; $R^4$ is $C_{1-6}$ alkyl; $R^5$ is hydrogen or $C_{1-6}$ alkyl; and $R^6$ or amino which comprises reacting a compound of formula (II) in which $R^1$, $R^4$ and $R^5$ are as defined in formula (I) and X is a leading group with a compound of formula (III).

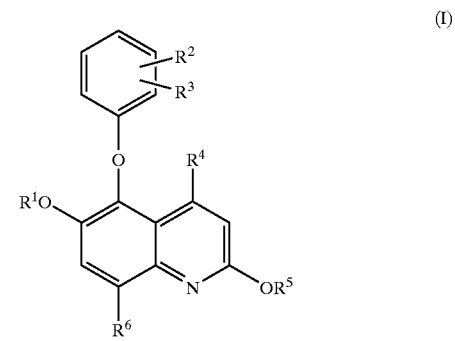

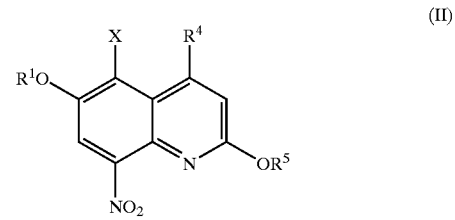

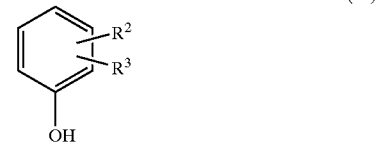

9 Claims, No Drawings

PROCESS FOR THE PREPARATION OF ANTI-MALARIAL DRUGS

This application is a 371 of PCT/EP96/04433, filed Oct. 11, 1996.

The present invention relates to novel processes for the preparation of compounds useful as anti-malarial drugs and novel intermediates useful in the process.

U.S. Pat. No. 4,617,394 discloses various compounds, including 8-(4-amino-1-methylbutylamino)-2,6-dimethoxy4-methyl-5-(3-trifluoromethylphenoxy)quinoline which are said to be useful as anti-malarial agents.

Key intermediates in the synthesis of the compounds of U.S. Pat. No. 4,617,394 are compounds of formula (I):

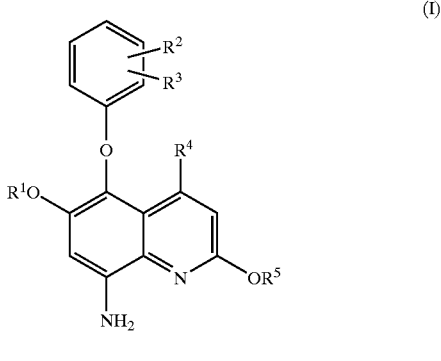

in which:

$R^1$ is $C_{1-6}$ alkyl;
$R^2$ and $R^3$ are independently hydrogen, halogen, trifluoromethyl or $C_{1-6}$ alkoxy;
$R^4$ is $C_{1-6}$ alkyl; and
$R^5$ is hydrogen or $C_{1-6}$ alkyl.

However the process disclosed in U.S. Pat. No. 4,617,394 for the preparation of this type of compound is a multi stage synthesis in which many steps proceed in low yield. A further disadvantage is that certain process steps use reagents which are not ideally suited to large scale synthesis. There is therefore a need for an improved procedure for the preparation of these intermediates and final anti-malarial compounds.

In a first aspect the present invention therefore provides a novel process for the preparation of a compound of formula (I)

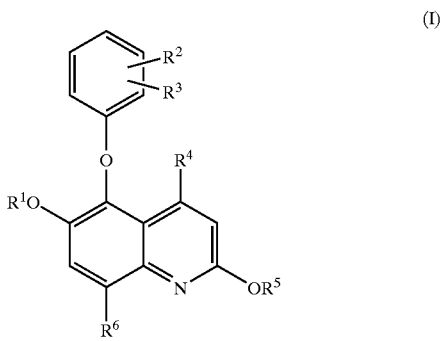

in which:

$R^1$ is $C_{1-6}$ alkyl;
$R^2$ and $R^3$ are independently hydrogen, halogen, trifluoromethyl or $C_{1-6}$ alkoxy;
$R^4$ is $C_{1-6}$ alkyl;
$R^5$ is hydrogen or $C_{1-6}$ alkyl; and
$R^6$ is nitro or amino which comprises reacting a compound of formula (II):

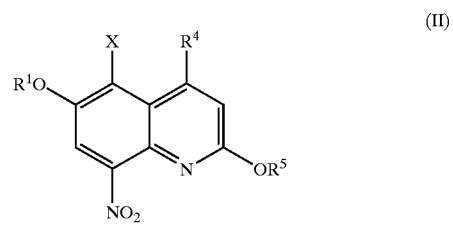

in which $R^1$, $R^4$ and $R^5$ are as defined in formula (I) and X is a leaving group with a compound of formula (III):

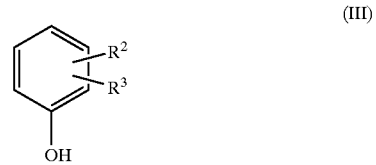

in which $R^2$ and $R^3$ are as defined in formula (I) and optionally thereafter:

converting the compound of formula (I) into another compound of formula (I)

Suitably X is a halogen, for example chloro. Preferably the reaction is carried out in the presence of base such as an alkali metal hydroxide at elevated temperature in a suitably inert solvent. Preferably the reaction is carried out using potassium hydroxide in DMSO at a temperature of about 105° C. to about 110° C.

A compound of formula (I) can be converted into another compound of formula (I) using standard procedures. For example compounds of formula (I) where $R^6$ is nitro can be converted to compounds of formula (I) where $R^6$ is amino by hydrogenation using gaseous hydrogen or a hydrogen donor in the presence of a metal catalyst. Preferably the reduction is carried out in the presence of a hydrogen donor and metal catalyst. Preferably the hydrogen donor is hydrazine hydrazine hydrate and the catalyst is Palladium on carbon. Preferably the reduction is carried out in an organic solvent such as ethanol, THF, toluene or mixtures thereof Most preferably the reaction is carried out in ethanol at elevated temperature, for example at reflux temperature.

Another example is where $R^5$ is hydrogen when compounds of formula (I) can be converted to compounds of formula (I) where $R^5$ is methoxy by chlorination followed by treatment with sodium methoxide.

Preferably the reaction is used to prepare the compound 8-nitro-2,6-dimethoxy-5-(3-trifluoromethyl)phenoxy-4-methylquinoline.

Certain compounds of formula (I) are believed to be novel. In a further aspect the invention therefore provides a compound of formula (IA):

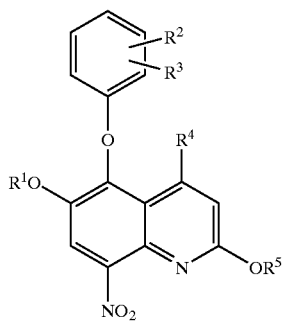

(IA)

in which:

R$^1$ is C$_{1-6}$ alkyl;

R$^2$ and R$^3$ are independently hydrogen, halogen, trifluoromethyl or C$_{1-6}$ alkoxy;

R$^4$ is C$_{1-6}$ alkyl; and

R$^5$ is hydrogen or C$_{1-6}$ alkyl.

Preferably for compounds of formula (I)/(IA) R$^1$, R$^4$ and R$^5$ are all methyl. Preferably R$^2$ is hydrogen and R$^3$ is trifluoromethyl, most preferably R$^3$ is in the 3-position of the phenyl ring relative to the ether linkage.

Preferred compounds of formula (IA) include 8-nitro-2,6-dimethoxy-5-(3-trifluoromethyl)phenoxy-4-methylquinoline.

Compounds of formula (II) can be prepared by nitration of a compound of formula (IV):

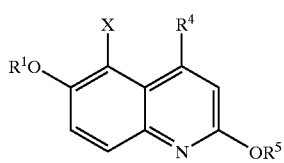

(IV)

in which R$^1$, R$^4$ and R$^5$ are as defined in formula (I) using standard nitration conditions. For example nitration can be carried out using concentrated nitric and sulphuric acid, or when R$^5$ is alkyl, using potassium nitrate in the presence of phosphorous pentoxide.

Compounds of formula (IV) are commercially available or can be prepared using standard procedures. For example compounds of formula (IV) where R$^4$ is methyl and X is chloro can be prepared using chemistry shown in the scheme shown below:

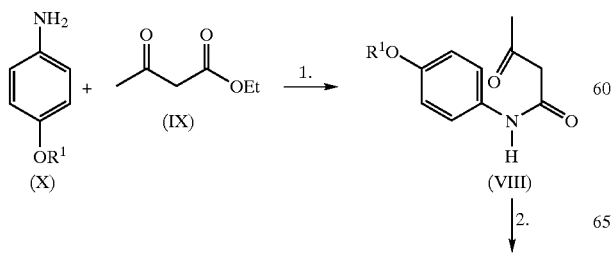

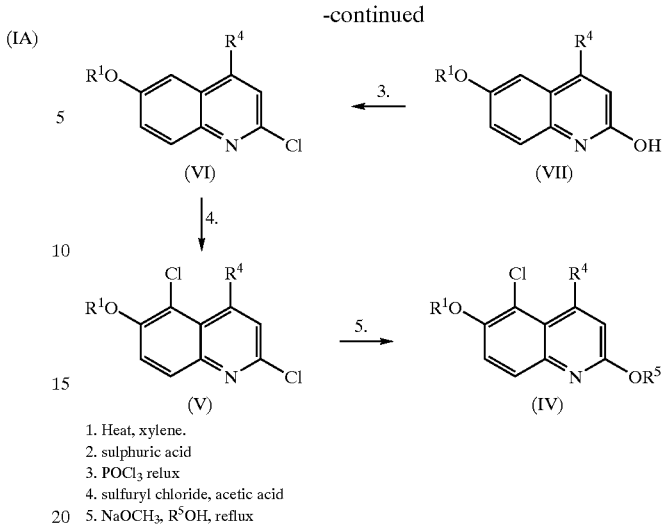

1. Heat, xylene.
2. sulphuric acid
3. POCl$_3$ relux
4. sulfuryl chloride, acetic acid
5. NaOCH$_3$, R$^5$OH, reflux Alternatively, compounds of formula (VI) can be converted to compounds of formula (IV) by addition of the methoxy group followed by chlorination using the above conditions. Compounds of formula (IX) and (X) are commercially available. Certain intermediates of formulae (II) and (IV) are novel and form a further aspect of the invention.

As mentioned above compounds of formula (I) are useful for the preparation of certain anti-malarial agents, in particular for the preparation of 8-[(4-amino-1-methylbutyl)amino]-2,6-dimethoxy-4-methyl-5-(3-trifluoromethylphenoxy)quinoline. In a further aspect the invention provides a process for the preparation of a compound of formula (A):

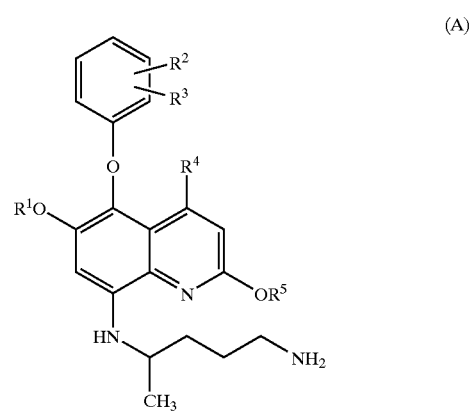

(A)

which comprises:
1. reacting a compound of formula (II):

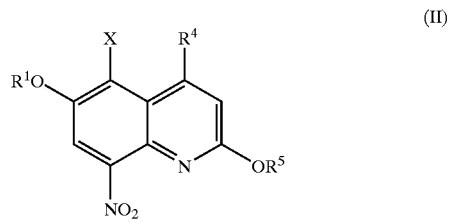

(II)

in which R$^1$, R$^4$ and R$^5$ are as defined in formula (I) and X is a leaving group with a compound of formula (III):

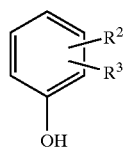

(III)

in which $R^2$ and $R^3$ are as defined in formula (I), followed by reduction of the nitro group to give a compound of formula (I) as hereinbefore defined where $R^6$ is amino; and 2. reacting said compound of formula (I) with a compound of formula (XI):

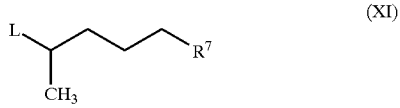

(XI)

where L is a leaving group and $R^7$ is amino or a protected amino group and optionally thereafter:
removing any protecting group;
forming a pharmaceutically acceptable salt.

Suitably L is a leaving group such as halogen such as bromo or iodo and $R^7$ is a protected amino group. Preferably L is iodo. Examples of appropriate protecting groups are well known in the art and include phthalimido, boc, t-boc and sulphonamide protecting groups. Preferred protecting groups include phthalimido.

Compounds of formulae (I) and (XI) are suitably reacted in the presence of a base, particularly an organic base, in an inert solvent system. For example a suitable base is diisopropylamine in NMP as solvent. Preferably the reaction is carried out at elevated temperature, for example at about 80° C. when NMP is used as solvent.

Protecting groups can be removed using procedures known in the art. For example phthalimide groups can be removed using hydrazine hydrate in an alcohol solvent at elevated temperature, for example in ethanol at reflux.

Compounds of formula (XI) can be prepared using standard chemistry as exemplified herein.

In a further aspect the present invention provides the use of the above processes for the preparation of 8-(4-amino-1-methylbutylamino)-2,6-dimethoxy4-methyl-5-(3-trifluoromethylphenoxy)quinoline and salts thereof. In a still further aspect the present invention provides the use of compounds of formulae (II) and (III) for the preparation of 8-(4-amino-1-methylbutylamino)-2,6-dimethoxy4-methyl-5-(3-trifluoromethylphenoxy)quinoline and salts thereof.

Pharmaceutically acceptable salts can be prepared using standard procedures. The compounds of the formula (I) can form acid addition salts with acids, such as conventional pharmaceutically acceptable acids, for example maleic, succinic, hydrochloric, hydrobromic, phosphoric, acetic, fumaric, salicylic, citric, lactic, mandelic, tartaric and methanesulphonic acids.

Preferred compounds of formula (A) which can be prepared using the procedures herein include 8-[(4-amino-1-methylbutyl)amino]-2,6-dimethoxy-4-methyl-5-(3-trifluoromethylphenoxy) quinoline. In another aspect the invention provides 8-[(4-amino-1-methylbutyl)amino]-2,6-dimethoxy-4-methyl-5-(3-trifluoromethylphenoxy) quinoline or a salt thereof prepared according to the procedures herein.

The invention will now be illustrated by the following examples.

EXAMPLE 1 p-Acetoanisidine

A 10-liter four necked reactor equipped with a mechanical stirrer, condenser, thermowatch and addition funnel was charged with ethylacetoacetate (870 g, 6.69 moles), triethanolamine (18 ml, 0.136 moles) and 2 liters of xylene. The solution was heated to reflux and a warm solution of p-anisidine (745 g, 6.15 moles) in 2 liters of xylene was added over 1.5 hours while continuously removing 2 liters of xylene by distillation. The resulting solution was heated at reflux for 1 hour, then slowly cooled to 70° C. 2 liters of hexane was slowly added over a 0.5 hour period, with stirring to bring it to room tempearture. The reaction mixture was further cooled to 0–5 ° C. in an ice bath for 3 hours. The product was removed by suction filtration, washed with 2 liters of hexane, air dried, and oven dried at 60° C. for 3–4 hours in an oven to yield 1.09 kg (87%) of the title compound, mp 105–108° C.; $^1$H-NMR(DMSO$_{d6}$): δ 10.0 (1, br s), 7.65 (1, dd, $J_o$=9 Hz, $J_m$=2 Hz), 7.48 (1, dd, $j_o$=9 Hz, $J_m$=2 Hz), 6.98 (1, dd, $J_o$=9 Hz, $J_m$=2 Hz), 6.85 (1, dd, $J_o$=9 Hz, $J_m$=2 Hz), 3.62 (3, s), 3.53 (2, s), 2.25 (3, s).

Analytically pure sample was obtained as white plates by recrystalisation from ethanol; mp 115–116° C. (lit[1] mp; 116–117° C.).

EXAMPLE 2

6-Methoxy4-methyl-2-quinolone

A 10-liter four-necked reactor equipped with a mechanical stirrer, thermowatch, and condenser was charged with 2.4 liters of concentrated sulphuric acid (96%), cooled to 15° C. and triethanolamine (40 g) added. p-Acetoanisidine (1) (3.3 kg, 15.9 moles) was added over 1 hour at 15–20. The resulting mixture was slowly heated to 90° C. over 1 hour, and at 90–95° C. for 5.5 hours. The hot syrup was poured slowly into a mechanically stirred water (5-liters). After stirring and cooling the mixture to room temperature, the solid was removed by suction filtration and washed with water. The slurry was resuspended in water, basified to pH 10 with concentrated ammonium hydroxide and stirred for thirty minutes. The product was removed by suction filtration, washed with water to neutral pH, and dried in vacuo at 90° C. to yield 1.95 kg (65%) of the title compound, mp 270–273° C. (lit[2]mp 273–274° C. from methanol).

$^1$H-NMR(TFA): δ 7.90 (1, d, $J_o$=9 Hz, H-8), 7.81 (1, dd, $J_o$=9 Hz, $J_m$=2 Hz, H-7), 7.58 (1, s, H-5), 7.30 (1, s, H-3), 4.12 (3, s, OCH$_3$), 2.91 (3, s, CH$_3$).

EXAMPLE 3

6-Methoxy-4-methyl-2-chloroquinoline

A 1-liter, four necked round bottom flask equipped with a mechanical stirrer, thermowatch, and condenser was charged with 630 grams (383 ml) of phosphorous oxychloride. The solution was heated to 50° C. and 6-methoxy-4-methyl-2-quinolone (2) (164.5 g, 0.87 moles) was added over 20 minutes. The reaction mixture was heated to reflux and held there for 2 hours. The hot reaction mixture was slowly poured into ice water (2.5 liters) and the resulting solution cooled to 30° C. The product was removed by suction filtration, washed with water and air dried to yield the title compound 156 g (86.4%); mp 144–145° C. (Lit[2] mp 143.5–144.5° C.);

$^1$H-NMR(TFA) δ 8.20 (1, d, $J_0$=9 Hz, H-8), 7.95 (1, s, H-5), 7.90 (1, dd, $J_0$=9 Hz, $J_m$=2 Hz, H-7), 7.68 (1, d, H-3), 4.22 (3, s, OCH$_3$), 3.08 (3, s, CH$_3$).

EXAMPLE 4

2,5-Dichloro-6-methoxy4-methylquinoline Hydrochloride

A 10-liter, four-necked reactor equipped with a mechanical stirrer, condenser, thermowatch, addition funnel and a condenser was charged with 6-methoxy-4-methyl-2-chloroquinoline (3) (900 g, 4.33 moles) and glacial acetic acid (3.06 liters). The slurry was heated to 60° C. and a solution of sulfuryl chloride (646 g, 4.77 moles) in glacial acetic acid (0.902 liters) was added over 2 hours while maintaining the temperature between 60 and 65° C. The resulting slurry was stirred for 1 hour at 60–65° C., then cooled to 15–20° C. and stirred at this temperature for 2 hours. The product was removed by suction filtration, washed with cold (10° C.) acetic acid (0.550 liters), and air dried. to yield the title compound 978.4 g (81.2%); mp 159–160° C. (dec).

$^1$H-NMR(TFA): δ 8.37 (1, d, $J_o$=9 Hz, H-8), 8.0 (1, d, $J_o$=9 Hz, H-7), 7.85 (1, s, H-3), 4.21 (3, s, OCH$_3$), 3.48 (3, s, CH$_3$).

EXAMPLE 5

2,6-Dimethoxy-5-chloro-4-methylquinoline

Method A

A 3-liter, four necked round bottom flask equipped with a mechanical stirrer, condenser, and thermowatch was charged with 2,5-dichloro-6-methoxy-4-methylquinoline hydrochloride (4) (170 g, 0.60 moles) and methanol (1 liter). A 25% methanolic solution of sodium methoxide (659 g, 3.05 moles) was added over 30 minutes. The resulting slurry was refluxed for 24 hours. Methanol (500 ml) was removed by atmospheric distillation, then, the heating mantle was removed and 500 ml of water was added slowly. The resulting slurry was cooled to 10° C. and the product collected by suction filtration, washed with water and air dried to yield the title compound 134 g (92.6%); mp 101–102° C.

$^1$H-NMR(TFA): δ 7.90 (2, s, H-8 and H-7), 7.43 (1, s, H-3), 4.43 (3, s, C-8 OCH$_3$), 4.12 (3, s, C-2 OCH$_3$), 3.38 (3, s, CH$_3$).

Method B

I) 2,6-Dimethoxy-4-methylquinoline

A 1-liter, four-necked round bottom flask equipped with a mechanical stirrer, condenser, thermowatch and addition funnel was charged with 6-methoxy-4-methyl-2-chloroquinoline (3) (20.75 g, 0.1 moles) and methanol (250 ml). Methanolic sodium methoxide (25%, 108 g, 0.5 moles) was added over 15 minutes. The resulting mixture was heated to reflux and held for 24 hours. Additional methanolic sodium methoxide was added (25%, 42 g, 0.2 moles) and the reaction was refluxed an additional 21 hours. The mixture was cooled to 60° C. and water (200 ml) was added slowly. The slurry was cooled to 10° C., the product isolated by suction filtration, washed with water, and air dried. Yield was 17.9 g (88.2%); mp=58–59° C.; purity by HPLC=100 area %.

$^1$H-NMR(TFA): δ 7.96(1, d, $J_o$=9 Hz, H-8), 7.75(1, dd, $J_o$=9 Hz, $J_m$=2 Hz, H-7), 7.63 (1, s, H-5), 7.44 (1, s, H-3), 4.41(3, s, OCH$_3$ C-6), 4.10(3, s, OCH$_3$ C-2), 3.00 (3,s, CH$_3$).

II) 2,6-Dimethoxy-5-Chloro-4-methylquinoline

A 500 ml, four-necked round bottom flask equipped with a mechanical stirrer, condenser, thermowatch and addition funnel was charged with 2,6-dimethoxy-4-methylquinoline (9) (17.9 g, 0.09 moles) and glacial acetic acid (120 ml). The resulting solution was heated to 60° C., then a solution containing sulfuryl chloride (13.4 g, 0.01 moles) and glacial acetic acid (40 ml) was added over 20 minutes. Reaction temperature was held between 60–65° C. during this addition. The resulting solution was stirred for 1 hour at 60–65° C., then additional sulfuryl chloride (3.8 g, o,028 moles) in glacial acetic acid (10 ml) was added. The mixture was stirred an additional 30 minutes, then it was poured into 300 ml of water. The slurry was cooled to 5° C., the product removed by suction filtration, washed with water and air dried. Yield was 18.4 g (86%); mp=97–100° C.; purity by HPLC=89.7 area %.

Method C

A 10-liter, five necked reactor equipped with a mechanical stirrer, condenser, and thermowatch was charged with 25% methanolic solution of sodium methoxide (2,29 kg, 10.6 moles) and N-methyl-2-pyrrolidone (1 liter). 2,5-dichloro-6-methoxy-4-methylquinoline hydrochloride (4) (1.0 kg, 3.59 moles) was added in portions over 1 hour during which the temperature of the reaction mixture reached 70° C. The temperature was maintained at 70° C. for 4 hours and then reduced to 50° C. and quenched with water (3.5 liters) slowly added over a period of 30 minutes with stirring. The product was collected by suction filtration, washed with water, air dried and oven dried at 50–55° C. to yield the title compound 0.81 kg (95%); mp 98–101° C.

$^1$H-NMR(CDCl$_3$): δ 7.69 (1, d, J=8.8 Hz, H-8), 7.26 (1, d, J=9.3 Hz, H-7), 6.63 (1, s, H-3), 3.98 (3, s, C-2 OCH$_3$), 2.9 (3, s, CH$_3$)

EXAMPLE 6

8-Nitro-2,6-dimethoxy-5-chloro-4-methylquinoline

A 20-liter reactor equipped with a mechanical stirrer, thermowatch, and condenser was charged with triethylphosphate (6.3 liters) and 2,6-dimethoxy-5-chloro-4-methylquinoline (5) (500 g, 2.11 moles). Phosphorous pentoxide (1.052 kg, 7.11 moles) was added in one portion and the resulting slurry stirred for 60 minutes. Reaction temperature was adjusted to 35° C. and solid potassium nitrate (0.423 kg, 4.21 moles) added in one portion. N-hexane is added and the reaction temperature was maintained at 35–40° C. for 2 hours. Methanol (4.2 liters) was added and the mixture heated to reflux and held for 1 hour. The yellow slurry was cooled to 0–5° C. and held for 2 hours. The product was collected by suction filtration, washed with water to neutral pH, then methanol, air dried and oven dried at 60–70° C. to yield the title compound 350 g (68%); mp 199–200° C.;

$^1$H-NMR(TFA): δ 8.75 (1, s, H-7), 7.63 (1, s, H-3), 4.55 (3, s, C-6 OCH$_3$), 4.24 (3,s, C-2 OCH$_3$), 3.40 (3, s, CH$_3$).

EXAMPLE 7

8-Nitro-2,6-dimethoxy-5-(3-trifluoromethyl) phenoxy-4-methylquinoline

Method A

A 500 ml, four necked round bottom flask equipped with a mechanical stirrer, thermowatch and condenser was charged with dimethyl sulfoxide (130 ml), m-trifluorophenol (24.8 g, 0.153 moles) and potassium hydroxide (8.5 g, 0.153 moles). The mixture was heated to 100° C. and held until all the potassium hydroxide had dissolved (about thirty minutes). Solid 8-nitro-2,6-dimethoxy-5-chloro-4-methylquinoline (6) (37.5 g, 0.133 moles) was added in one portion and the resulting dark solution was held for 2.5 hours at 100° C. Water (250 ml) was added slowly while holding the temperature above 60° C. The resulting slurry was cooled to 10° C. and the product removed by suction filtration, washed with water and dried in vacuo to give a crude yield of the title compound 50.5 g (93.3%); mp 188–190° C.

The crude product was dissolved in 700 ml of refluxing toluene and stirred with Darco KB (5 g). After filtration through celite, toluene (500 ml) was removed by distillation followed by cooling to 70° C. and dilution with 500 ml of hexane. This resulting slurry was cooled to 0–5° C. and the product collected by suction filtration, washed with hexane, and air dried to yield the title compound 47.3 g (87.2%); mp 194–196° C.; NMR(CDCl$_3$): δ 7.84 (1, s, H-7), 7.4–6.8 (4, br multiplet, phenoxy ring), 6.83 (1, s, H-3), 4.05 (3, s, C-6 OCH$_3$), 3.84 (3, s, C-2 OCH$_3$), 2.65 (3, s, CH$_3$).

Method B

I) 6-Methoxy-5-chloro-4-methyl-2-quinolone

In a 250 ml, three-necked round bottom flask equipped with a mechanical stirrer, thermowatch, and addition funnel was placed glacial acetic acid (125 ml) and 6-methoxy-4-methyl-2-quinolone (15.78 g, 0.0834 moles). This was heated to 70° C., then a solution of sulfuryl chloride (13.5 g, 0.100 moles) and glacial acetic acid (10 ml) was added over 50 minutes. Reaction temperature held between 70–75° C. and product precipitated from solution about one third through the addition. The slurry was stirred for 15 minutes, then cooled to ambient temperature. Product was isolated by suction filtration followed by two 20 ml washes with acetic acid and one 50 ml wash with ethanol. Air dried yield is 17.9 g; purity by HPLC is 76.6 area % (contains 9.8% starting material and 12.8% over chlorinated product)

This crude product was recrystallized from 850 ml of boiling ethanol, to which 2 ml of concentrated ammonium hydroxide was added, and the solution was filtered hot. This clear solution was cooled to room temperature, then held at 0° C. over night. Air dried yield is 12.2 g (65.4%); mp=235–237° C.; purity by HPLC=91.2 area %.

$^1$H-NMR(TFA): δ 7.93 (1, d, J$_o$=9 Hz, H-8), 7.78 (1, d, J$_o$=9 Hz), 7.28 (1, s, H-3), 4.18 (3, s, OCH$_3$), 3.28 (3, s, CH$_3$).

II) 8-Nitro-6-methoxy-5-chloro-4-methyl-2-quinolone

In a 200 ml, three-necked round bottom flask equipped with a mechanical stirrer, thermowatch, and addition funnel was placed 96% sulfuric acid (50 ml) and 6-methoxy-5-chloro-4-methyl-2-quinolone (10) (12.0 g, 53.66 mmoles). This was cooled to 0° C., then a solution of 70% nitric acid(6.04 g, 67.1 mmoles) in 96% sulfuric acid (10 ml) was added dropwise over 35 minutes. The mixture was stirred for 90 minutes at 0° C., then poured into 350 ml of water. The crude orange-brown solid was collected by suction filtration, washed with water (three×20 ml) and air dried. Crude yield is 10.82 g.

The solid was dissolved in hot 2-ethoxyethanol (114), cooled to ambient temperature, then cooled to 0° C. an d held for 30 minutes. The orange solid was removed by suction filtration, washed with 20 ml of 2-ethoxyethanol, and air dried. Yield is 5.6 g (38.9%); mp=201–204° C.; purity by HPLC=96.4 area %;

$^1$H-NMR(TTA): δ 8.67 (1, s, H-7), 7.36 (1, s, H-3), 4.25 (3, s, OCH$_3$), 3.25 (3, s, CH$_3$).

III) 8-Nitro-6-methoxy-5-(3-trifluoromethyl)phenoxy-4-methyl-2-quinolone

In a 50 ml, three necked round bottom flask equipped with a thermowatch and magnetic stirrer was placed n-methylpyrrolidinone (20 ml), solid potassium hydroxide (87.2%, 1.42 g, 21.84 mmoles) and m-trifluoromethylcresol (3.54 g, 21.84 mmoles). This was heated to 100° C. and stirred until all the potassium hydroxide dissolved (30 minutes). Solid 8-nitro-6-methoxy-5-chloro-4-methyl-2-quinolone (11) (5.35 g, 19.9 mmoles) was added and the reaction was held at 100° C. for 1 hours. The mixture was poured into water (250 ml) and this was extracted three times with 150 ml of ethyl acetate. The combined organic layer was back extracted with water, dried over anhydrous magnesium sulfate, filtered and concentrated to dryness on a Rotary Evaporator. Crude yield 6.8 g (84.5%)

Crude product was dissolved in 70 ml of boiling methanol, cooled to 0° C., filtered and washed two times with 10 ml of methanol. Yield is 3.85 g; mp=153–155° C. $^1$H-NMR(CDCl$_3$) δ 8.25 (1, s, H-7), 7.6–6.8 (4, br multiplet, Phenoxy ring), 6.58 (1, s, H-3), 3.81 (3, s, OCH$_3$), 2.58 (3, s, CH$_3$).

IV) 8-Nitro-6-methoxy-5-(3-trifluoromethyl)phenoxy-4-methyl-2-chloroquinoline

In a 50 ml three-necked round bottom flask equipped with a thermowatch and magnetic stirrer was placed phosphorous oxychloride (5 ml) and 8-nitro-6-methoxy-5-(3-trifluoromethyl)phenoxy-4-methyl-2quinolone (12) (4.75 g, 12.0 mmoles). This was refluxed for forty five minutes, then the hot syrup was cautiously poured into 200 ml of water. After cooling the slurry to ambient temperature, the product was removed by suction filtration, washed twice with 20 ml of water and air dried. Yield was 4.89 g (99%); mp=227–232° C.;

$^1$H-NMR(TFA): δ 9.11 (1, s, H-7), 8.10 (1, s, H-3), 7.7–7.1 (4, br multiplet, Phenoxy ring), 4.02 (3, s, OCH$_3$), 3.27 (3, s, CH$_3$).

V) 8-Nitro-2,6-dimethoxy-5-(3-trifluoromethyl)phenoxy-4-methylquinoline

In a 500 ml three-necked round bottom flask equipped with a mechanical stirrer, thermowatch, and condenser was placed methanol (130 ml), tetrahydrofuran (50 ml), 8-nitro-6-methoxy-5-(3-trifluoromethyl)phenoxy-4-methyl-2-chloroquinoline (13) (4.80 g, 11.36 mmoles) and 25% methanolic sodium methoxide (9.83 g, 38.4 mmoles). This was refluxed for 18 hours, then the cooled reaction mix was poured into 250 ml of water. The yellow product was removed by suction filtration, washed with water (20 ml) and air dried. Yield was 4.45 g (93.7%).

EXAMPLE 8

8-Amino-2,6-dimethoxy-5-(3-trifluoromethyl) phenoxy-4-methylquinoline

A 500 ml, four-necked round bottom flask equipped with a mechanical stirrer, thermowatch, condenser, and addition funnel was charged with 8-nitro-2,6-dimethoxy-5-(3-trifluoromethyl)phenoxy-4-methylquinoline (7) (16.32 g, 0.04 moles), anhydrous ethanol (100 ml) and 5% palladium on carbon (50% wet, 250 mg). The mixture was heated to 60° C., then hydrazine hydrate (20.0 g, 0.2 moles) was added slowly over 15 minutes. The mixture was held at 60° C. for 4 hours, then refluxed for thirty minutes. After cooling to 50° C. catalyst was removed by filtration through celite, and washed with ethanol (40 ml). Water (100 ml) was slowly added to the ethanol filtrate over thirty minutes the resulting slurry cooled to 5° C., the product collected by suction filtration. After washing with 50 ml of 1:1 ethanol/water the solid was dried to yield the title compound 13.8 g (91.3%); mp=116–117° C. (lit[3] mp=114–117° C.); $^1$H-NMR (DMSO$_{d6}$): δ 7.6–7.1 (4, br multiplet, Phenoxy ring, 7.03 (1, s, H-7), 6.85 (1, s, H-3), 5.88 (2, br s, NH2), 4.02(3, s, C-6 OCH$_3$), 3.80 (3, s, C-2 OCH$_3$), 2.53 (3, s, CH$_3$).

EXAMPLE 9

8-[(4-Amino-1-methylbutyl)amino]-2,6-dimethoxy-4-methyl-5-(3-trifluoromethylphenoxy)quinoline succinate I) 4-bromo-1-phthalimidopentane A one liter, four necked round bottom flask equipped with a mechanical stirrer, thermowatch and condenser was charged with acetone (500 ml), potassium phthalimide (92.5 g, 0.5 moles) and 1,4-dibromopentane (153 g, 0.665 moles). The resulting mixture was refluxed for 24 hours (HPLC showed 2.5% unreacted phthalimide), then cooled to 15° C. Solid sodium bromide was removed by suction filtration and one wash of the cake with acetone (50 ml). The solvent was removed using a rotary evaporator to give 187.2 g of a crude viscous yellow oil. Excess 1,4-dibromopentane (34.5 g) was removed by vacuum distillation at 35–40° C./0.3 mm of pressure, leaving 144.6 g (97.7%) of a yellow viscous oil.

$^1$H-NMR (CDCl$_3$): d8.0–7.5 (4, multiplet, benzene ring), 4.5–3.9 (1, br multiplet, C-4), 3.9–3.5 (2, multiplet, C-1), 2.0–1.7 (4, multiplet, C-2 and C-3), 1.70 (3, d, CH$_3$).

II) 4-iodo-1-phthalimidopentane

A two liter, four necked round bottom flask equipped with a mechanical stirrer, thermowatch and condenser was charged with 4-bromo-1-phthalimidopentane (14) (122.6 g, 0.414 moles), acetone (850 ml) and sodium iodide (73.5 g, 0.49 moles). The reaction was refluxed for 23 hours. HPLC analysis of the mixture showed 5% unreacted bromo compound 14 remaining. The mixture was cooled to 15° C. and the precipitated solid (sodium bromide) was removed by suction filtration and washed three times with acetone (100 ml). The combined organic solution was concentrated to dryness using a rotary evaporator. Methylene chloride (500 ml) was added to the residue. Additional solid formed (sodium iodide) and this was removed by suction filtration and washed with 100 ml of methylene chloride. The combined methylene chloride solution was washed successively with 5% sodium bisulfite (1×500ml) and water (500 ml), then dried over magnesium sulfate. The methylene chloride was removed using a rotary evaporator, leaving a viscous yellow oil. Yield was 149 g (104.5%). Attempts to crystallize the material from petroleum ether failed. Purity by HPLC was only 41.4%. A further check by TLC (Merck silica gel 60 F254 5×10 cm eluted with methylene chloride) showed two spots of almost equal intensity. $^1$H-NMR (CDCl$_3$): d7.9–7.5(4, multiplet, benzene ring), 4.5–3.9 (1, br multiplet, C-4), 3.8–3.4(2, multiplet, C-2), 1.90 (3, d, CH$_3$), 1.9–1.5 (4, multiplet, C-2 and C-3) This crude material was used as is. Purity was assumed to be about 85% based on the NMR.

III) 8-[(4-Phthalimido-1-methylbutyl) amino]-2,6-dimethoxy-4-methyl-5-(3-trifluoromethylphenoxy)quinoline A 25 ml, three necked round bottom flask equipped with a thermowatch, condenser, and magnetic stirrer was charged with 8-amino-2,6-dimethoxy-4-methyl-5-(3-trifluoromethylphenoxyquinoline (8) (1.89 g, 5 mmoles), 4-iodo-1-phthalimidopentane (15) (2.0 g, 5 mmoles at 85% assumed purity), diisopropylamine (0.55 g, 5.5 mmoles) and n-methylpyrrolidinone (5 ml). The resulting mixture was heated at 80° C. for 6 hours, then additional 4-iodo-1-phthalimidopentane (1.5 g, 3.75 mmoles) and diisopropylamine (0,39 g, 3.8 mmoles) were added. This mixture was then held at 80° C. for a total of 24 hours. HPLC of the reaction mixture showed 1.6 area % unreacted aminoquinoline (8), so the reaction was cooled to room temperature. Water (10 ml) was added slowly, causing the product to separate as a viscous gum. The solvent was removed by decantation and isopropanol (15 ml) was added. The mixture was heated to reflux and allowed to cool slowly (about 1 hour) to room temperature. A yellow-brown solid formed. This slurry was cooled to 0–5° C., held for 1 hour, and the product was removed by suction filtration and washed once with cold isopropanol (5 ml). The product was air dried to give 2.27 g (76.6%), mp=117–119° C. Recrystallization from isopropanol (6 volumes) gives a 93% recovery of product (2.1 g) with a mp of 119–120° C.

$^1$H-NMR(CDCl3): d7.9–7.5(4, multiplet, benzene ring), 7.4–6.8 (4, multiplet, phenoxy ring), 6.64 (1, s, C-7), 6.55 (1, s, C-3), 4.00 (3, s, C-6 OCH$_3$), 3.9–3.4(3, multiplet, side chain). 3.80 (3, s, C-3 OCH$_3$), 2.53 (3, s, CH$_3$), 2.0–1.5 (4, multiplet, side chain), 1.35 (3, d, side chain CH$_3$).

IV) 8-[(4-Amino-1-methylbutyl)amino]-2,6-dimethoxy-4-methyl-5-(3-trifluoromethylphenoxy)quinoline succinate A 50 ml, three necked round bottom flask equipped with a magnetic stirrer, condenser and thermowatch was charged with 8-[(4-phthalimido-1-methylbutyl)amino]-2,6-dimethoxy-4-methyl-5-(3-trifluoromethylphenoxy)quinoline (16) (1.186 g, 2 mmoles), 95% ethanol (12 ml) and hydrazine monohydrate (0.425 g, 8.5 mmoles. The reaction was refluxed for 30 minutes, then a large amount of solid formed (phthalhydrazide). Ethanol (8 ml) was added to dilute the reaction and this was refluxed for an additional 30 minutes. HPLC showed the reaction was complete, so the heat was removed and the reaction cooled to 20–25° C. The solid was removed by suction filtration and washed with ethanol (4×5 ml). The combined ethanol solution was concentrated to dryness using a rotary evaporator to give 0.9 g of crude title compound as the free base. This crude product was dissolved in methylene chloride (50 ml) and washed twice with 25 ml of 25% potassium hydroxide solution and washed once with 25 ml of water. The organic layer was dried over magnesium sulfate and concentrated to dryness using a rotary evaporator. The residue was dissolved in acetonitrile (5 ml) and a warm solution containing succinic acid (0.23 g, 2.3 mmoles), methanol (0.5 ml) and acetonitrile (5 ml) was added. The resulting solution was stirred and allowed to cool to room temperature and held for about 3–4 hours. The product was removed by suction filtration, washed with acetonitrile (5 ml) and air dried. Yield of off-white solid was 0.72 g (61.9%), mp=146–149° C.

$^1$H-NMR(DMSO$_{d6}$): δ 8.45 (4, br singlet, exchanges with D$_2$O, NH$_2$ and COOH), 7.6–6.8 (4, multiplet, phenoxy ring), 7.15 (1, s, C-7), 6.80 (1, s, C-3), 4.03(3, s, C-6 OCH$_3$), 3.85 (3, s, C-3 OCH$_3$), 3.2–2.6 (2, br multiplet, C-1 of side chain), 2.55 (3, s, CH$_3$), 2,0–1.5 (4, br multiplet, C-2 and C-3 of side-chain), 1.33 (3, d, CH$_3$ of side chain).

References

1. K. N Campbell, R. S. Tipson, R. C. Elderfield, B. K. Campbell, M. A. Clapp, W. J. Gensler, D. Morrison, and W. J. Moran, *J. Org. Chem.*, 1946, 11, 803.
2. L. C. March, W. A. Romanchick, G. S. Bajaw, and M. M. Joullié, *J. Med. Chem*, 1973, 16, 337.
3. M. P. LaMontagne, P. Blumbergs, D. C. Smith, *J. Med Chem*, 1989, 32, 1728.

What is claimed is:

1. A process for the preparation of a compound of formula (I)

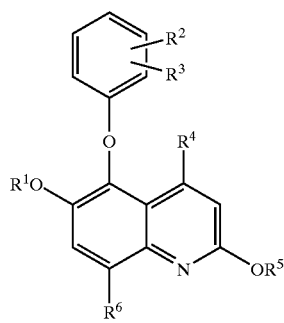

in which:

$R^1$ is $C_{1-6}$ alkyl;

$R^2$ and $R^3$ are independently hydrogen, halogen, trifluoromethyl or $C_{1-6}$ alkoxy;

$R^4$ is $C_{1-6}$ alkyl;

$R^5$ is hydrogen or $C_{1-6}$ alkyl; and $R^6$ is nitro or amino which comprises reacting a compound of formula (II):

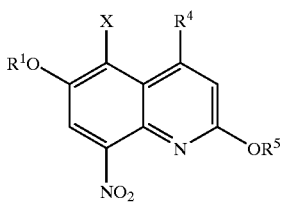

in which $R^1$, $R^4$ and $R^5$ are as defined in formula (I) and X is a leaving group with a compound of formula (III):

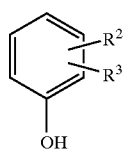

in which $R^2$ and $R^3$ are as defined in formula (I) and optionally thereafter:

converting the compound of formula (I) into another compound of formula (I).

2. A process according to claim 1 in which $R^1$, $R^4$ and $R^5$ are all methyl.

3. A process according to claim 1 in which $R^2$ is hydrogen and $R^3$ is trifluoromethyl.

4. A process according to claim 1 where X is halogen.

5. A process according to claim 1 in which the compound of formula (I) is 8-nitro-2,6-dimethoxy-5-(3-trifluoromethyl)phenoxy-4-methylquinoline.

6. A compound of formula (IA):

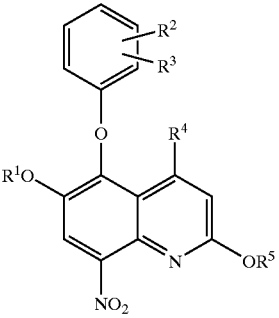

in which:

$R^1$ is $C_{1-6}$ alkyl;

$R^2$ and $R^3$ are independently hydrogen, halogen, trifluoromethyl or $C_{1-6}$ alkoxy;

$R^4$ is $C_{1-6}$ alkyl; and $R^5$ is hydrogen or $C_{1-6}$ alkyl.

7. A compound according to claim 6 which is 8-nitro-2,6-dimethoxy-5-(3-trifluoromethyl)phenoxy-4-methylquinoline.

8. A process for the preparation of a compound of formula (A):

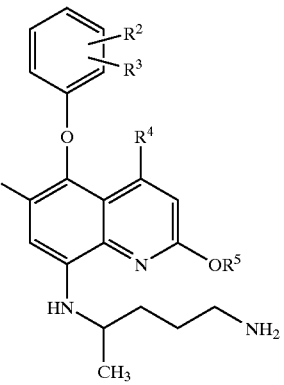

wherein:

$R^1$ is $C_{1-6}$ alkyl;

$R^2$ and $R^3$ are independently hydrogen, halogen, trifluoromethyl or $C_{1-6}$ alkoxy;

$R^4$ is $C_{1-6}$ alkyl;

$R^5$ is hydrogen or $C_{1-6}$ alkyl; and $R^6$ is nitro or amino;

which comprises:

1. reacting a compound of formula (II):

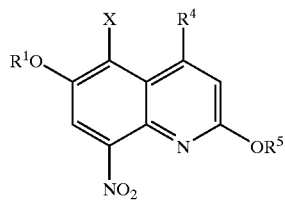
(II)

wherein X is a leaving group, with a compound of formula (III):

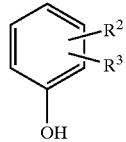
(III)

followed by reduction of the nitro group to give a compound of formula (I):

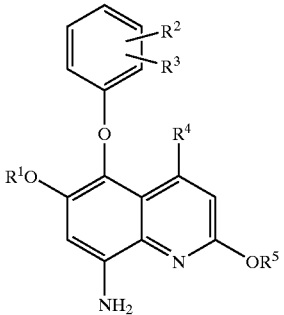
(I)

where $R^6$ is amino; and 2. reacting said compound of formula (I) with a compound of formula (XI):

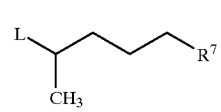
(XI)

where L is a leaving group and $R^7$ is amino or a protected amino group and optionally thereafter:
removing any protecting group;
forming a pharmaceutically acceptable salt.

9. A process according to claim 8 in which the compound prepared is 8-[(4-amino-1-methylbutyl)amino]-2,6-dimethoxy-4-methyl-5-(3-trifluoromethylphenoxy) quinoline or a pharmacautically acceptable salt thereof.

* * * * *